(12) United States Patent
Chen et al.

(10) Patent No.: US 6,210,716 B1
(45) Date of Patent: Apr. 3, 2001

(54) CONTROLLED RELEASE BUPROPION FORMULATION

(75) Inventors: Chih-Ming Chen; Jianbo Xie, both of Davie; Steve Jan, Coral Springs, all of FL (US)

(73) Assignee: Andrx Pharmaceuticals, Inc., Fort Lauderdale, FL (US)

( * ) Notice: Subject to any disclaimer, the term of this patent is extended or adjusted under 35 U.S.C. 154(b) by 0 days.

(21) Appl. No.: 09/259,133

(22) Filed: Feb. 26, 1999

(51) Int. Cl.[7] .............................. A61K 9/14; A61K 9/52; A61K 9/58

(52) U.S. Cl. ........................... 424/497; 424/489; 424/490

(58) Field of Search ..................... 424/489, 490

(56) References Cited

U.S. PATENT DOCUMENTS

| | | | |
|---|---|---|---|
| Re. 33,994 | 7/1992 | Baker et al. | 424/465 |
| 2,011,587 | 8/1935 | Miller | 167/82 |
| 2,987,445 | 6/1961 | Levesque | 167/82 |
| 3,143,463 | 8/1964 | Holm et al. | 167/22 |
| 3,146,169 | 8/1964 | Stehenson et al. | 167/82 |
| 3,538,214 | 11/1970 | Polli et al. | 424/19 |
| 3,773,920 | 11/1973 | Nakamoto et al. | 424/19 |
| 3,819,706 | 6/1974 | Mehta | 260/570.5 |
| 3,885,046 | 5/1975 | Mehta | 424/330 |
| 4,016,880 | 4/1977 | Theeuwes et al. | 128/260 |
| 4,060,598 | 11/1977 | Groppenbächer et al. | 424/33 |
| 4,116,241 | 9/1978 | Theeuwes et al. | 128/260 |
| 4,135,514 | 1/1979 | Zaffaroni et al. | 128/260 |
| 4,256,108 | 3/1981 | Theeuwes | 128/260 |
| 4,309,405 | 1/1982 | Guley et al. | 424/21 |
| 4,327,725 | 5/1982 | Cortese et al. | 128/260 |
| 4,393,078 | 7/1983 | Peck | 424/330 |
| 4,439,194 | 3/1984 | Harwood et al. | 604/890 |
| 4,439,196 | 3/1984 | Higuchi | 604/890 |
| 4,507,323 | 3/1985 | Stern | 514/451 |
| 4,519,801 | 5/1985 | Edgren | 604/892 |
| 4,539,198 | 9/1985 | Powell et al. | 424/19 |
| 4,557,925 | 12/1985 | Lindahl et al. | 424/19 |
| 4,571,395 | 2/1986 | Peck | 514/221 |
| 4,769,027 | 9/1988 | Baker et al. | 424/493 |
| 4,798,826 | 1/1989 | Peck | 514/221 |
| 4,935,429 | 6/1990 | Dackis et al. | 514/288 |
| 5,071,646 | 12/1991 | Malkowska et al. | 424/497 |
| 5,098,715 | 3/1992 | McCabe et al. | 424/429 |
| 5,358,970 | 10/1994 | Ruff et al. | 514/649 |
| 5,427,798 | * 6/1995 | Ludwig et al. | 424/464 |
| 5,472,708 | * 12/1995 | Chen | 424/451 |
| 5,508,040 | * 4/1996 | Chen | 424/451 |
| 5,541,231 | 7/1996 | Ruff et al. | 514/649 |
| 5,731,000 | 3/1998 | Ruff et al. | 424/451 |
| 5,763,493 | 6/1998 | Ruff et al. | 514/617 |

OTHER PUBLICATIONS

Physcians"Desk Reference, 47th Edition 1993, pp. 842–844.

* cited by examiner

*Primary Examiner*—Jose' G. Dees
*Assistant Examiner*—Konata M. George
(74) *Attorney, Agent, or Firm*—Hedman & Costigan, P.C.

(57) ABSTRACT

A controlled release dosage form of bupropion hydrochloride which comprises:

(a) a first pellet having a core of bupropion hydrochloride and hydroxypropyl methylcellulose at a weight ratio of 10:1 to 30:1 and a coating of a mixture of an acrylic resin which is soluble in acidic media and ethyl cellulose;

(b) a second pellet having a core of bupropion hydrochloride and hydroxypropyl methylcellulose at a ratio of 10:1 to 30:1; an inner coating of a mixture of an acrylic resin which is soluble in acidic media and a water insoluble polymer and an outer coating which comprises an enteric coating polymer.

12 Claims, No Drawings

CONTROLLED RELEASE BUPROPION FORMULATION

BACKGROUND OF THE INVENTION

The present invention relates to a controlled release formulation of bupropion hydrochloride. The compound bupropion hydrochloride is described in U.S. Pat. No. 3,819,706 as an antidepressant.

U.S. Pat. No. 5,427,798 describes a controlled release formulation of bupropion which based on a ratio of hydroxypropyl methylcellulose which is 1 part of bupropion to 0.19 to 1.1 parts of hydroxypropyl methylcellulose. U.S. Pat. No. 5,358,970 discloses a formulation of bupropion hydrochloride which is stabilized with a stabilizer which has specific acid properties under particular test conditions. RE 33,994 is limited to a bupropion hydrochloride controlled release formulation which releases 10–45% of bupropion hydrochloride within two hours; 25–70% bupropion hydrochloride within 4 hours and 40–90% of bupropion hydrochloride within six hours. Wellbutrin SR is a commercially available twice a day dosage form of bupropion hydrochloride which contains carnauba wax, cysteine hydrochloride, hydroxypropyl methylcellulose, magnesium stearate, microcrystalline cellulose, polyethylene glycol and titanium dioxide.

The applicants have discovered that a two pellet controlled release formulation may be employed to provide a dosage formulation which has a controlled release profile which is bioequivalent to Wellbutrin SR but has a distinctly different in vitro release profile than Wellbutrin SR.

SUMMARY OF THE INVENTION

The present invention provides a novel dosage form of bupropion hydrochloride which comprises:

(a) a first pellet having a core which comprises bupropion hydrochloride and hydroxypropyl methylcellulose at a weight ratio of 10:1 to 30:1 and a coating which comprises a mixture of an acrylic resin which is soluble in acidic media and ethyl cellulose;

(b) a second pellet having a core which comprises bupropion hydrochloride and hydroxypropyl methylcellulose at a ratio of 10:1 to 30:1, preferably 20:1; an inner coating which comprises a mixture of an acrylic resin which is soluble in acidic media and a water insoluble polymer and an outer coating which comprises an enteric coating polymer.

Generally, the weight ratio of the first pellet to the second pellet will be from 90:10 to 30:70 although a weight ratio of 80:20 is preferred.

Accordingly, it is a primary object of this invention to provide a pharmaceutical dosage formulation of bupropion which is suitable for twice a day administration.

It is also an object of this invention to provide a hydrogel-free pharmaceutical dosage form of bupropion hydrochloride which is bioequivalent to dosage forms of bupropion hydrochloride which have a hydrogel component.

It is also an object of this invention to provide a stable dosage form of bupropion hydrochloride which is based on a two pellet-membrane coated dosage form.

These and other objects of the invention will become apparent from a review of the appended specification.

DETAILED DESCRIPTION OF THE INVENTION

The bupropion hydrochloride formulation of the invention is preferably based on active pellets having a core forming inert component which may comprise non-pareil sugar seeds (sugar spheres, USP XXII) having an average size of from 14 to 35 mesh, preferably about 30 to 35 mesh. The core forming inert component is coated with a formulation which comprises bupropion hydrochloride and hydroxypropyl methylcellulose. A sufficient amount of the coating is applied to provide the dosage of bupropion hydrochloride, i.e. 50 mg to 300 mg.

To form pellet A, the active pellet is then coated with a seal coat which may comprise a mixture of hydroxypropyl methylcellulose and polyethylene glycol. The hydroxypropyl methylcellulose may have a viscosity of 5 mPa's at a 2 wt % conc. in water at 20° C. The polyethylene glycol may have a number average molecular weight of from 200 to 2000 although a number average molecular weight of 400 is preferred. Generally a ratio of 2:1 to 6:1 of hydroxypropyl methylcellulose to polyethylene glycol may be applied as a 3 to 7 wt % solution in a solvent such as ethanol, isoporopyl alcohol, water, mixtures therof and the like.

The seal coat is then coated with a release modifying coating which comprises a mixture of an acrylic resin which is soluble in acidic media and a water insoluble polymer. The water insoluble polymer may comprise a cellulosic polymer such as ethylcellulose, cellulose acetate and the like. The release modifying seal coating may comprise a weight ratio of acrylic resin which is soluble in acidic media to water insoluble polymer of about 1:4 which is applied from a 3 to 7 wt % solution of isopropyl alcohol, ethanol, acetone, mixtures therof and the like to form a coating.

A useful acrylic resin which is soluble in acidic media is Eudragit E which is a cationic copolymer of dimethylaminoethyl methacrylate and neutral methacrylic acid esters having a mean weight average molecular weight of 150,000.

If desired a seal coat of a film forming polymer such as polyvinyl pyrrolidone, hydroxypropyl cellulose, hydroxypropyl methylcellulose or the like may be applied to form a coating.

To form pellet B, pellet A is coated with a first coating of hydroxypropyl methylcellulose which is applied from a 5 wt % solution of ethanol, water or mixtures thereof to form a coating. An enteric coating is then placed on the coating of the hydroxypropyl methylcellulose. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate, polyvinyl acetate phthalate or mixtures thereof. Cellulose acetate phthalate is preferred. The thickness of the coating is selected to provide the desired release rate depending on the thickness of the coating and the particular coating. The enteric coating may be applied as a 3 to 7 wt % solution of the enteric polymer in acetone, ethanol, isopropyl alcohol or mixtures thereof.

Other auxiliary coating aids such as a minor amount (1–5 wt % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which is selected from the group consisting of an alkaline earth metal stearate, such as magnesium stearate or calcium stearate, or talc. The antisticking agents can be used alone or in combination.

The cores are formed by spraying the non-pareil seeds with an aqueous or non-aqueous suspension which contains the bupropion hydrochloride and the hydroxypropyl methylcellulose. The suspension medium may comprise any low viscosity solvent such as isopropyl alcohol, ethanol, water, mixtures thereof and the like. When fluids such as water are employed, this will usually require a weight of fluid which is about seven times the weight of the dry components of the coating composition.

It is preferred to dry each coating before applying a second coating. A color imparting agent may be added to the enteric coating mixture or a rapidly dissolving seal coat containing color may be coated over the enteric coating layer provided that the seal coat is compatible with and does nor affect the dissolution of the enteric coating layer.

Pellets A and pellets B are blended together to obtain a finished product having the following in vitro release profile:

50 to 80 wt % released after 2 hours in SGF (pH 1.5);
70 to 95 wt % released after 4 hours in SGF (pH 1.5);
not less than 80 wt % released after 6 hours in SGF (pH 1.5);
as determined in a USPXXII Type 2 apparatus, at 37° C. and 50 rpm.

The pellets may be placed in a gelatin capsule or they may be made into tablets by first adding from 25 to 40 wt % of a solid pharmaceutically acceptable tablet excipient which will form a compressible mixture with pellets A and pellets B which may be formed into a tablet without crushing pellets A or pellets B, and optionally an effective amount of a tablet disintegrating agent and a lubricant. The solid pharmaceutically acceptable tablet excipient may comprise lactose, dextrose, mannitol, calcium phosphate, microcrystalline cellulose, kaolin, powdered sucrose or mixtures thereof. The tablet disintegrant may comprise crospovidone, croscarmellose sodium, dry starch, sodium starch glycolate and the like.

DESCRIPTION OF THE PREFERRED EMBODIMENTS

EXAMPLE 1

Active pellets of bupropion hydrochloride are formed by placing sugar spheres in a fluidized bed coater and spraying a suspension containing bupropion hydrochloride and hyroxypropyl methylcellulose onto the sugar spheres. The formulation for making the active pellets has the following composition:

| | |
|---|---|
| bupropion hydrochloride, Usp | 9760 g |
| hydroxypropyl methylcellulose E5 | 480 g |

The bupropion hydrochloride, hydroxypropyl methylcellulose and about 48,000 g of water and isopropyl alcohol (3:1) are mixed with a mechanical mixer until the materials are dissolved.

9760.0 g of non-pareil sugar spheres (NF 30/35 mesh) are placed in the fluidized bed coater and the suspension containing the bupropion is coated at a product temperature of 30–50° C.; an atomization pressure of 2–3.5 bar and a pump rate of 20–200 ml/minute, starting with a slow rate of pumping to avoid agglomeration and increasing the rate of pumping consistent with the avoidance of the formation of agglomerates.

After coating is complete the pellets are dried at a temperature of 50° C. until the loss on drying is less than 1 wt %. The pellets are then screened through a #18 mesh screen and coated with the following formulation:

| | |
|---|---|
| hydroxypropyl methylcellulose | 1342 g. |
| polyethylene glycol 400 | 335 g. |

After drying the pellets, a further coating is applied as follows:

| | |
|---|---|
| ethyl cellulose E100 | 4124 g. |
| acrylic polymer (Eudragit E-100 | 1694 g. |

The coated pellets are dried to complete the formation of pellets A.

Pellets B are formed by coating pellets B as follows:

| | |
|---|---|
| Pellets A | 11,000 g |
| hydroxypropyl methylcellulose | 256 g |

The hydroxypropyl methyl cellulose is dissolved in ethanol and applied to pellets A. Thereafter an enteric coating is applied as follows to form pellets B:

| | |
|---|---|
| cellulose acetate phthalate | 1228 g |
| acetyltributyl citrate | 307 g |

A tablet is made by blending:

| | |
|---|---|
| Pellets A | 51 parts by weight |
| Pellets B | 14 parts by weight |
| crospovidone XL-10 | 5 parts by weight |
| microcrystalline cellulose PH102 | 29 parts by weight |
| glyceryl monostearate | 1 parts by weight |

The tablets were compressed using a B-press tabletting machine, with a punch size of 0.4375".

The tablets were tested according to the USP XXII dissolution test (type 2, basket) at 50 rpm, at 37° in SGF (pH 1.5) to determine the percent of the drug dissolved versus time:

| Tablets | |
|---|---|
| Time (hr) | Percent Dissolved |
| 0.5 | 13 |
| 1.0 | 32 |
| 2.0 | 62 |
| 4.0 | 83 |
| 6.0 | 92 |
| 8.0 | 98 |
| Pellets A | |
| 0.5 | 6 |
| 1.0 | 40 |
| 2.0 | 91 |
| 4.0 | 98 |

-continued

Tablets

| Time (hr) | Percent Dissolved |
|---|---|
| 6.0 | 100 |
| 8.0 | 100 |
| Pellets B | |
| 0.5 | 0 |
| 1.0 | 0 |
| 2.0 | 1 |
| 4.0 | 16 |
| 6.0 | 54 |
| 8.0 | 73 |

All of the components which are used in the present invention are used in amounts which are effective for the intended purpose for which the component is employed.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A controlled release dosage form of bupropion hydrochloride which comprises:
   (a) a first pellet having a core which comprises bupropion hydrochloride and hydroxypropyl methylcellulose at a weight ratio of 10:1 to 30:1 and a coating which comprises a mixture of an acrylic resin which is soluble in acidic media and ethyl cellulose;
   (b) a second pellet having a core which comprises bupropion hydrochloride and hydroxypropyl methylcellulose at a ratio of 10:1 to 30:1; an inner coating which comprises a mixture of an acrylic resin which is soluble in acidic media and a water insoluble polymer and an outer coating which comprises an enteric coating polymer.

2. A controlled release dosage form of bupropion hydrochloride as defined in claim 1 wherein the pellets are combined in a capsule.

3. A controlled release dosage form of bupropion hydrochloride as defined in claim 1 wherein the pellets are combined in a tablet.

4. A controlled release dosage form of bupropion hydrochloride as defined in claim 1 wherein the weight ratio of the first pellets to the second pellets is from 90:10 to 30:70.

5. A controlled release dosage form of bupropion hydrochloride as defined in claim 3 wherein
   the tablet comprises the first pellets, the second pellets and a solid pharmaceutically acceptable diluent.

6. A controlled release dosage form of bupropion hydrochloride as defined in claim 3 wherein
   the first pellets are formed on a core which comprises a sugar sphere.

7. A controlled release dosage form of bupropion hydrochloride as defined in claim 1 wherein
   the first pellets are formed on a core which comprises a sugar sphere.

8. A controlled release dosage form of bupropion hydrochloride as defined in claim 1 wherein
   the second pellets have a seal coating between the inner coating which comprises a mixture of an acrylic resin which is soluble in acidic media and a water insoluble polymer and the enteric coating.

9. A controlled release dosage form of bupropion hydrochloride as defined in claim 1 wherein
   the second pellets have an enteric coating which is selected from the group consisting of methacrylic acid copolymers, cellulose acetate phthalate, hydroxypropylmethylcellulose phthalate, hydroxypropylmethylcellulose acetate succinate, cellulose acetate trimellitate and polyvinyl acetate phthalate.

10. A controlled release dosage form of bupropion hydrochloride as defined in claim 1 wherein
    the second pellets have an enteric coating which comprises cellulose acetate phthalate.

11. A controlled release dosage form of bupropion hydrochloride which comprises:
    (a) a first pellet having a core which is a sugar sphere coated with a mixture comprising bupropion hydrochloride and hydroxypropyl methylcellulose at a weight ratio of 10:1 to 30:1 and a coating which comprises a mixture of acrylic resin and ethyl cellulose;
    (b) a second pellet having a core which is a sugar sphere coated with a mixture comprising bupropion hydrochloride and hydroxypropyl methylcellulose at a ratio of 10:1 to 30:1; an inner coating which comprises a acrylic resin which and ethyl cellulose and an outer coating which comprises cellulose acetate phthalate plasticized with acetyltributyl citrate.

12. A controlled release dosage form of bupropion hydrochloride as defined in claim 1 wherein the dosage form has the following in vitro release profile:
    50 to 80 wt % released after 2 hours in SGF (pH 1.5);
    70 to 95 wt % released after 4 hours in SGF (pH 1.5);
    more than 80 wt % released after 6 hours in SGF (pH 1.5);
    as determined in a USPXXII Type 2 apparatus, at 37° C. and 50 rpm.

* * * * *